(12) United States Patent
Yu et al.

(10) Patent No.: US 11,017,249 B2
(45) Date of Patent: May 25, 2021

(54) PRIMARY PREVIEW REGION AND GAZE BASED DRIVER DISTRACTION DETECTION

(71) Applicant: Futurewei Technologies, Inc., Plano, TX (US)

(72) Inventors: Hai Yu, San Jose, CA (US); Fatih Porikli, San Jose, CA (US); Yuzhu Wu, Sunnyvale, CA (US)

(73) Assignee: Futurewei Technologies, Inc., Plano, TX (US)

( * ) Notice: Subject to any disclaimer, the term of this patent is extended or adjusted under 35 U.S.C. 154(b) by 112 days.

(21) Appl. No.: 15/882,581

(22) Filed: Jan. 29, 2018

(65) Prior Publication Data
US 2019/0236386 A1 Aug. 1, 2019

(51) Int. Cl.
*G06K 9/00* (2006.01)
*A61B 5/00* (2006.01)
(Continued)

(52) U.S. Cl.
CPC ........ *G06K 9/00845* (2013.01); *A61B 5/0077* (2013.01); *A61B 5/18* (2013.01); *A61B 5/746* (2013.01); *B60W 10/18* (2013.01); *B60W 10/20* (2013.01); *B60W 30/09* (2013.01); *B60W 50/16* (2013.01); *G06F 3/013* (2013.01);
(Continued)

(58) Field of Classification Search
CPC .... G06K 9/00845; G06K 9/66; A61B 5/0077; A61B 5/18; A61B 5/746; B60W 10/18; B60W 10/20; B60W 30/09; B60W 50/16; G06F 3/013; H04N 5/33
See application file for complete search history.

(56) References Cited

U.S. PATENT DOCUMENTS 6,009,377 A * 12/1999 Hiwatashi ............ B62D 15/025
180/204
6,246,880 B1 * 6/2001 Iizuka ............... H04W 72/0486
455/446
(Continued)

FOREIGN PATENT DOCUMENTS

EP 3109114 A1 12/2016
JP 2010097335 A 4/2010
(Continued)

OTHER PUBLICATIONS

Google Scholar search results.*
(Continued)

*Primary Examiner* — Qun Shen
(74) *Attorney, Agent, or Firm* — Schwegman Lundberg & Woessner, P.A.

(57) ABSTRACT

A computer-implemented method of detecting distracted driving comprises: determining, by one or more processors, a primary preview region (PPR) in a representation of an environment; determining, by the one or more processors, a gaze point for a driver based on a sequence of images of the driver; determining, by the one or more processors, that the gaze point is outside of the PPR; based on the determined gaze point being outside of the PPR, decreasing, by the one or more processors, an attention level for the PPR; based on the attention level for the PPR, generating, by the one or more processors, an alert.

19 Claims, 13 Drawing Sheets

US 11,017,249 B2
Page 2

(51) Int. Cl.
*A61B 5/18* (2006.01)
*B60W 10/18* (2012.01)
*B60W 10/20* (2006.01)
*B60W 30/09* (2012.01)
*B60W 50/16* (2020.01)
*G06F 3/01* (2006.01)
*G06K 9/66* (2006.01)
*H04N 5/33* (2006.01)
*B60W 50/14* (2020.01)

(52) U.S. Cl.
CPC ............... *G06K 9/66* (2013.01); *H04N 5/33* (2013.01); *B60W 2050/143* (2013.01); *B60W 2540/00* (2013.01)

(56) References Cited

U.S. PATENT DOCUMENTS

| | | | |
|---|---|---|---|
| 2005/0073136 A1 | 4/2005 | Larsson et al. | |
| 2010/0033333 A1* | 2/2010 | Victor | A61B 5/1114 340/576 |
| 2011/0019570 A1* | 1/2011 | Leung | H04L 43/04 370/252 |
| 2012/0005135 A1* | 1/2012 | Miyano | G06K 9/6232 706/12 |
| 2013/0188838 A1 | 7/2013 | Tsou et al. | |
| 2014/0139655 A1* | 5/2014 | Mimar | G08B 21/06 348/77 |
| 2015/0194035 A1 | 7/2015 | Akiva et al. | |
| 2016/0098735 A1* | 4/2016 | Sinha | G06Q 30/0202 705/7.31 |
| 2017/0001648 A1* | 1/2017 | An | B60W 30/08 |
| 2017/0083746 A1 | 3/2017 | Kim | |
| 2017/0112463 A1* | 4/2017 | An | A61N 1/00 |
| 2017/0274906 A1* | 9/2017 | Hassan | B60K 28/14 |
| 2018/0012085 A1 | 1/2018 | Blayvas et al. | |
| 2019/0065638 A1* | 2/2019 | Sun | G06T 7/11 |

FOREIGN PATENT DOCUMENTS

| | | |
|---|---|---|
| WO | WO-2010104161 A1 | 9/2010 |
| WO | WO-2018006019 A1 | 1/2018 |

OTHER PUBLICATIONS

"International Application No. PCT/CN2019/072809, International Search Report and Written Opinion dated Apr. 24, 2019", (Apr. 24, 2019), 9 pgs.
Fletcher, Luke, et al., "Driver Inattention Detection based on Eye Gaze-Road Event Correlation", *The International Journal of Robotics Research*, 28(6)', (Jun. 2009), 774-801.
Liao, Yuan, et al., "Detection of Driver Cognitive Distraction: A Comparison Study of Stop-Controlled Intersection and Speed-Limited Highway", *IEEE Transactions on Intelligent Transportation Systems*, 17(6), (Jun. 2016), 1628-1637.
"European Application No. 19744456.5, Extended European Search Report dated Feb. 16, 2021", (Feb. 16, 2021), 10 pgs.
"India Application No. 202047033766, Examination report dated Mar. 16, 2021", (Mar. 16, 2021), 9 pgs.

\* cited by examiner

PPP TABLE

| ID | LOCATION | TYPE |
|---|---|---|
| 1 | (0, 0, 5) | VEHICLE |
| 2 | (3, -0.5, 20) | CURVE |
| 3 | (-1, 2, 12) | SIGN |

PPR TABLE

| ID | RELATIVE PPP LOCATION | SIZE |
|---|---|---|
| 1 | EDGE | 2 METER RADIUS |
| 2 | CENTER | 2 METER RADIUS |
| 3 | CENTER | 0.5 METER RADIUS |

ATTENTION LEVEL TABLE

| ID | ATTENTION LEVEL | GAZE STATUS | TIME OF LAST ATTENTION CHANGE | TRANSITION ATTENTION LEVEL |
|---|---|---|---|---|
| 1 | 0.75 | IN PPR | 12:25:32.43 | 0.60 |
| 2 | 0.52 | OUT OF PPR | 12:25:32.43 | 0.72 |
| 3 | 0.33 | OUT OF PPR | 12:25:30.20 | 0.54 |

DRIVER TABLE

| CURRENTLY ACTIVE | REACTION COEFFICIENT |
|---|---|
| TRUE | 1.0 |
| FALSE | 0.25 |

PRIMARY PREVIEW REGION AND GAZE BASED DRIVER DISTRACTION DETECTION

TECHNICAL FIELD

The present disclosure is related to gaze detection and, in one particular embodiment, to primary preview region and gaze based driver distraction detection.

BACKGROUND

Many accidents are caused by distracted drivers paying insufficient attention to the road and obstacles. These distracted-driving accidents cause substantial loss of lives as well as economic harm. In the United States, accidents are the fourth-leading cause of death.

SUMMARY

Various examples are now described to introduce a selection of concepts in a simplified form that are further described below in the Detailed Description. The Summary is not intended to identify key or essential features of the claimed subject matter, nor is it intended to be used to limit the scope of the claimed subject matter.

According to one aspect of the present disclosure, there is provided a computer-implemented method of detecting distracted driving that comprises: determining, by one or more processors, a primary preview region (PPR) in a representation of an environment; determining, by the one or more processors, a gaze point for a driver based on a sequence of images of the driver; determining, by the one or more processors, that the gaze point is outside of the PPR; based on the determined gaze point being outside of the PPR, decreasing, by the one or more processors, an attention level for the PPR; based on the attention level for the PPR, generating, by the one or more processors, an alert.

Optionally, in any of the preceding embodiments, the method further comprises: determining a second gaze point for the driver based on a second sequence of images of the driver; and based on the second gaze point being inside of the PPR, increasing the attention level for the PPR.

Optionally, in any of the preceding embodiments, the decreasing of the attention level for the PPR comprises determining the attention level using a logistic decay function.

Optionally, in any of the preceding embodiments, the PPR is a first PPR and is one of a plurality of PPRs, each PPR of the plurality of PPRs having a corresponding attention level; the generating of the alert is further based on the attention level for each PPR of the plurality of PPRs; and the method further comprises: estimating a future path using vehicle and road information; determining that the first PPR is not along the future path; and based on the determination that the first PPR is not along the future path, removing the first PPR from the plurality of PPRs.

Optionally, in any of the preceding embodiments, the method further comprises: determining a priority score for each PPR of the plurality of PPRs; and wherein the attention level for each PPR of the plurality of PPRs is based on the priority score for the PPR.

Optionally, in any of the preceding embodiments, the method further comprises: identifying, by one or more processors, an object depicted in the representation of the environment; and wherein the determining of the PPR comprises determining the PPR for the object.

Optionally, in any of the preceding embodiments, the determining of the PPR for the object comprises determining a velocity of the object.

Optionally, in any of the preceding embodiments, the identifying of the object depicted in the image of the environment comprises analyzing the image with a trained machine-learning algorithm.

Optionally, in any of the preceding embodiments, the determining of the PPR comprises: determining a primary preview point (PPP); and determining the PPR based on the PPP and a predetermined radius.

Optionally, in any of the preceding embodiments, the representation of the environment is generated by an infrared (IR) camera.

Optionally, in any of the preceding embodiments, the determining of the PPR in the representation of the environment comprises identifying a lane of a road.

Optionally, in any of the preceding embodiments, the representation of the environment is generated by a laser scanner.

Optionally, in any of the preceding embodiments, the generating of the alert comprises generating an audio alert.

Optionally, in any of the preceding embodiments, the generating of the alert comprises generating a haptic alert.

Optionally, in any of the preceding embodiments, the generating of the alert comprises activating brakes of a vehicle.

Optionally, in any of the preceding embodiments, the generating of the alert comprises altering a direction of a vehicle.

Optionally, in any of the preceding embodiments, the determining of the attention level for the PPR is based on a profile of the driver.

Optionally, in any of the preceding embodiments, the generating of the alert is further based on a predetermined threshold.

According to one aspect of the present disclosure, there is provided a system for detecting distracted driving that comprises: a memory storage comprising instructions; and one or more processors in communication with the memory, wherein the one or more processors execute the instructions to perform: determining a primary preview region (PPR) in a representation of an environment; determining a gaze point for a driver based on a sequence of images of the driver; determining that the gaze point is outside of the PPR; based on the determined gaze point being outside of the PPR, decreasing an attention level for the PPR; and based on the attention level for the PPR, generating an alert.

According to one aspect of the present disclosure, there is provided a non-transitory computer-readable medium that stores computer instructions for detecting distracted driving, that when executed by one or more processors, cause the one or more processors to perform steps of: determining a primary preview region (PPR) in a representation of an environment; determining a gaze point for a driver based on a sequence of images of the driver; determining that the gaze point is outside of the PPR; based on the determined gaze point being outside of the PPR, decreasing an attention level for the PPR; and based on the attention level for the PPR, generating an alert.

Any one of the foregoing examples may be combined with any one or more of the other foregoing examples to create a new embodiment within the scope of the present disclosure.

BRIEF DESCRIPTION OF THE DRAWINGS

FIG. 9 is a block diagram illustrating a database schema suitable for gaze-based driver detection using primary preview regions, according to some example embodiments.

DETAILED DESCRIPTION

Figure 1:
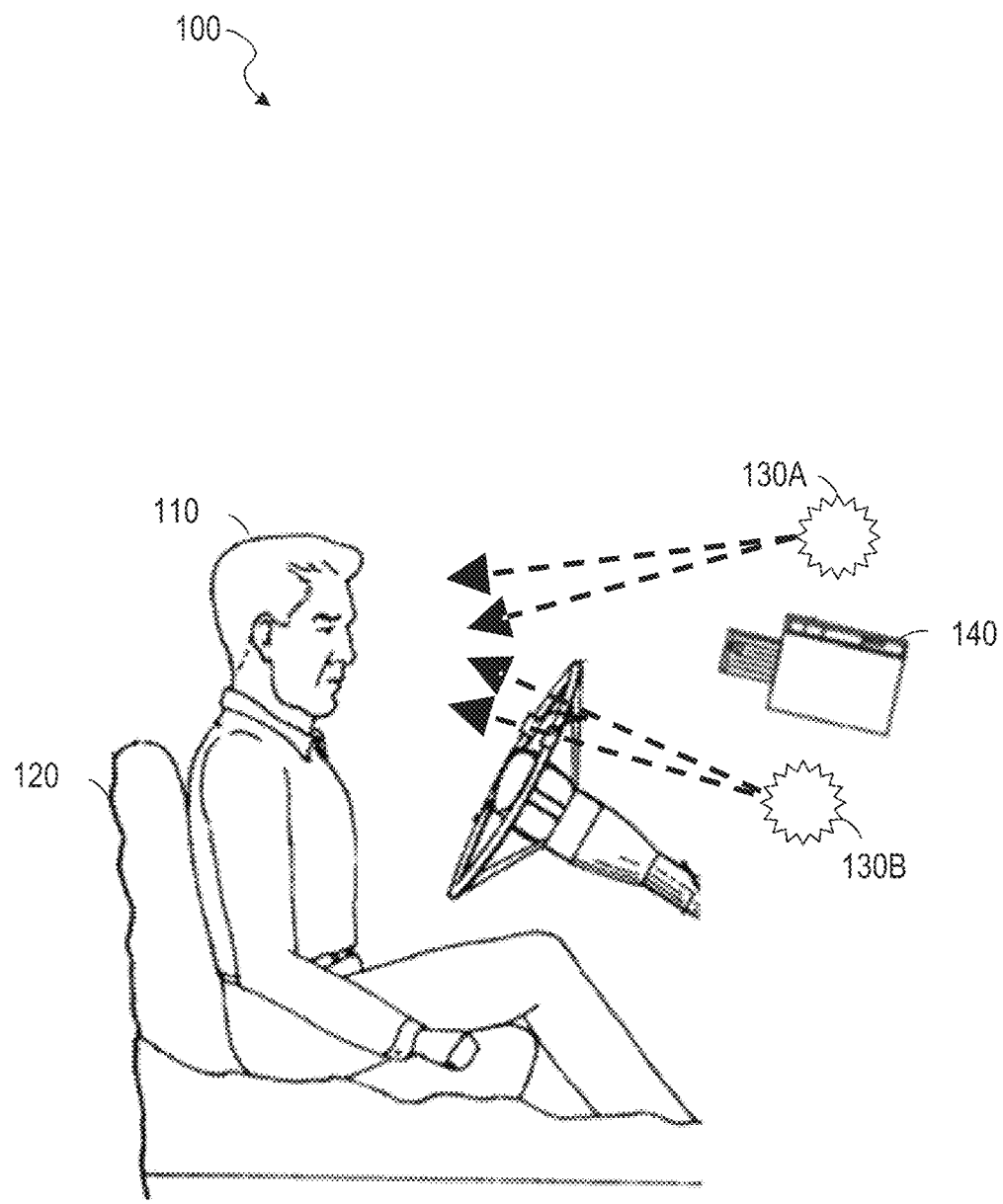
FIG. 1 is an illustration of a vehicle interior, according to some example embodiments.

In the following description, reference is made to the accompanying drawings that form a part hereof, and in which are shown, by way of illustration, specific embodiments which may be practiced. These embodiments are described in sufficient detail to enable those skilled in the art to practice the inventive subject matter, and it is to be understood that other embodiments may be utilized and that structural, logical, and electrical changes may be made without departing from the scope of the present disclosure. The following description of example embodiments is, therefore, not to be taken in a limiting sense, and the scope of the present disclosure is defined by the appended claims.

The functions or algorithms described herein may be implemented in software, in one embodiment. The software may consist of computer-executable instructions stored on computer-readable media or a computer-readable storage device such as one or more non-transitory memories or other types of hardware-based storage devices, either local or networked. The software may be executed on a digital signal processor, application-specific integrated circuit (ASIC), programmable data plane chip, field-programmable gate array (FPGA), microprocessor, or other type of processor operating on a computer system, turning such a computer system into a specifically programmed machine. The computer system may be integrated into a vehicle.

A vehicle may include one or more external cameras that capture images of the environment of the vehicle. The cameras may be visible-light cameras, infrared (IR) cameras, laser scanners, or any suitable combination thereof. The captured images may be converted to a three-dimensional (3D) representation of the environment or processed as a two-dimensional (2D) representation of the environment.

The representation of the environment is analyzed (e.g., by a trained machine learning algorithm) to identify one or more primary preview points (PPPs) or primary preview regions (PPRs). A PPP is a particular point to which the driver should pay attention. A PPR is a region to which the driver should pay attention. A PPP may be located within a corresponding PPR. The term PPR will be used herein to discuss both PPPs and PPRs, unless otherwise noted. PPRs may be identified for any object (e.g., a vehicle, animal, pedestrian, sign, pothole, bump, cone, or fallen tree), region (e.g., a vanishing point of a lane, or a curve in a road), or situation (e.g., an accident, a mudslide, or flooding) that a driver should pay attention to.

The vehicle may also include a driver-facing camera that captures images of the driver. Using the captured images of the driver in conjunction with the captured images of the environment, a gaze detection system determines a focus point of the driver. The focus point of the driver is compared to each of the PPRs to determine if the driver is focusing on the PPP or PPR.

An attention level may be generated for each PPR that indicates a degree of attention being paid to the PPR. During time periods in which the driver's focus is on the PPR, the attention level for the PPR is increased. During time periods in which the driver's focus is not on the PPR, the attention level for the PPR is decreased. If the attention level for the PPR falls below a predetermined threshold, an alert is generated. Example alerts include highlighting the PPR on a heads-up display (HUD) of the vehicle, a visual alert in the form of a flashing light, providing haptic feedback via a steering wheel, providing an audio alert, automatically engaging brakes, automatically steering the vehicle to avoid the ignored PPR, parking the vehicle, or any suitable combination thereof.

By use of the systems and methods described herein, a vehicle may alert a distracted driver to an object, region, or situation that the driver otherwise would have failed to see and react to. By virtue of the alert, the distracted driver may react to the object, region, or situation and avert an accident. Accordingly, use of the systems and methods described herein improves vehicle safety.

FIG. 1 is an illustration of a vehicle interior 100, according to some example embodiments. Shown in the vehicle interior 100 is an illustration of a driver 110, a seat 120, light sources 130A and 130B, and a camera 140. The light sources 130A-130B and the camera 140 may be controlled by a computer system such as that described below with respect to FIG. 8.

The light sources 130A-130B may be near infrared (IR) light sources. The camera 140 may be receptive to wavelengths of light provided by the light sources 130A-130B (e.g., near IR) and be focused on the driver 110. Images captured by the camera 140 may be used to determine the direction and focus depth of the eyes of the driver 110 based on glints generated by the light generated by the light sources 130A-130B reflecting off of the surface of the eyes of the driver 110. Headpose, the orientation of the driver's head, may also be determined from images captured by the camera 140 and used in determining the direction and focus depth of the driver's gaze. Additionally, the camera 140 may detect hand gestures by the driver 110.

The camera 140 may comprise a depth camera that captures stereoscopic images to determine distance of objects from the camera. For example, two near IR image sensors may be used to determine a three-dimensional headpose or to detect a gesture that involves moving toward or away from the camera 140. As another example, a time-of-flight camera may be coordinated with the light sources 130A and 130B and determine depth based on the amount of time between emission of light from a light source and receipt of the light (after reflection from an object) at the time-of-flight camera.

Figure 2:
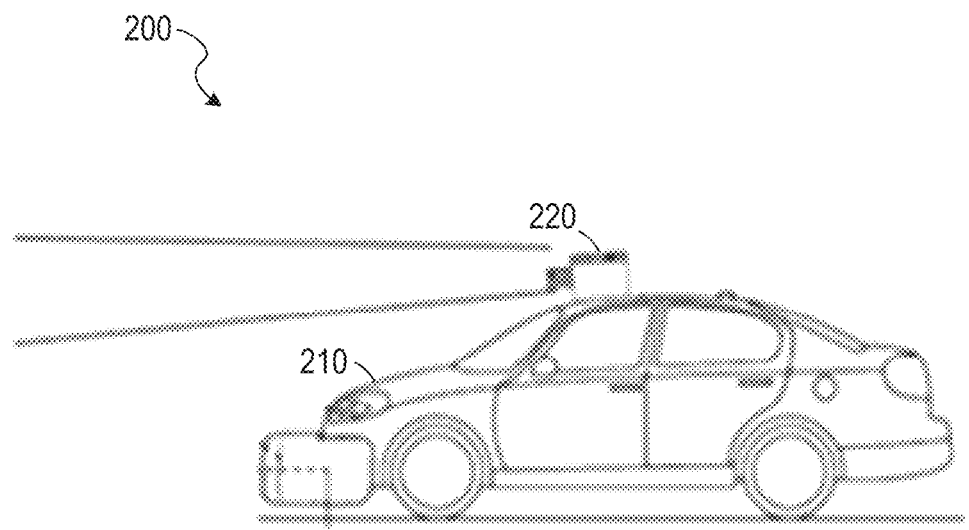
FIG. 2 is an illustration of a vehicle exterior, according to some example embodiments.

FIG. 2 is an illustration 200 of a vehicle exterior, according to some example embodiments. The illustration 200 includes the vehicle 210 and the camera 220. The camera 220 is mounted on the roof of the vehicle 210 and may be a second camera controlled by the same system controlling the first camera, the camera 140 of FIG. 1. The camera 220 may be a wide-angle camera, a 360 degree camera, a rotating camera, or any suitable combination thereof. The camera 220 may be integrated into the vehicle 210 (e.g., sold by the manufacturer as part of the vehicle 210 and permanently attached to the rest of the vehicle 210), securely mounted to the vehicle 210 (e.g., by bolts or screws), or temporarily attached to the vehicle 210 (e.g., by being placed in a holder on a dashboard). The vehicle 210 is an automobile, but the invention is not so limited and may be used with other vehicles such as aircraft, watercraft, or trains.

Figure 3:
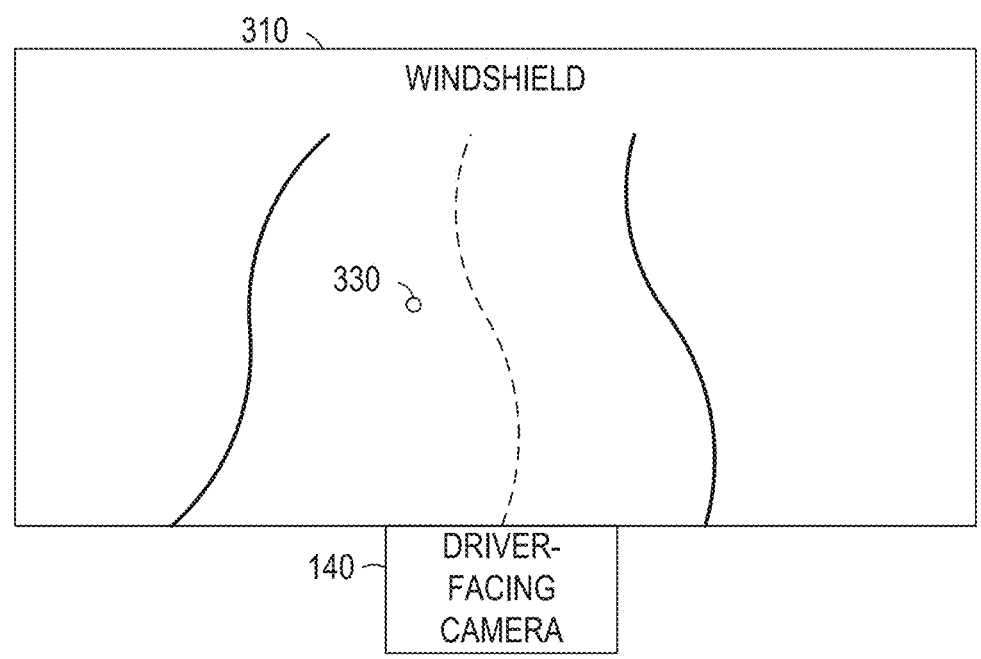
FIG. 3 is an illustration of an example gaze detection point of a driver's gaze through a windshield, according to some example embodiments.

FIG. 3 is an illustration of an example gaze detection point 330 of a driver's gaze through a windshield 310, according to some example embodiments. Also shown in FIG. 3 is the driver-facing camera 140.

The driver-facing camera 140 captures one or more images of the driver of a vehicle. For each captured image, the driver's eyes are identified and a focus point of the driver's gaze is determined. The focus point is a point in three-dimensional space. For example, an angle between the location of a pupil and a centerline of an eye may be determined for each eye. Rays may be traced from the center of each eye through the pupil to determine an intersection point of the focus of the two eyes. A representation of the environment of the vehicle may be compared with the intersection point to determine the position of the gaze detection point 330 in the environment.

When the representation of the environment is a 2D representation, such as a 2D image captured by the camera 220, the gaze detection point 330 may be determined by projecting a 3D gaze angle to the 2D image based on camera calibration. The camera calibration aligns the coordinate system of the camera that captures the driver's face (e.g., the camera 140) with the coordinate system of the camera that captures the environment (e.g., the camera 220). Camera calibration may be performed by asking the driver to focus on known points and using the measurements of the driver's gaze to update the calibration values. For example, the center of the steering wheel, the corners of the windshield, and the rear-view mirror may be used as known points.

Figure 4:
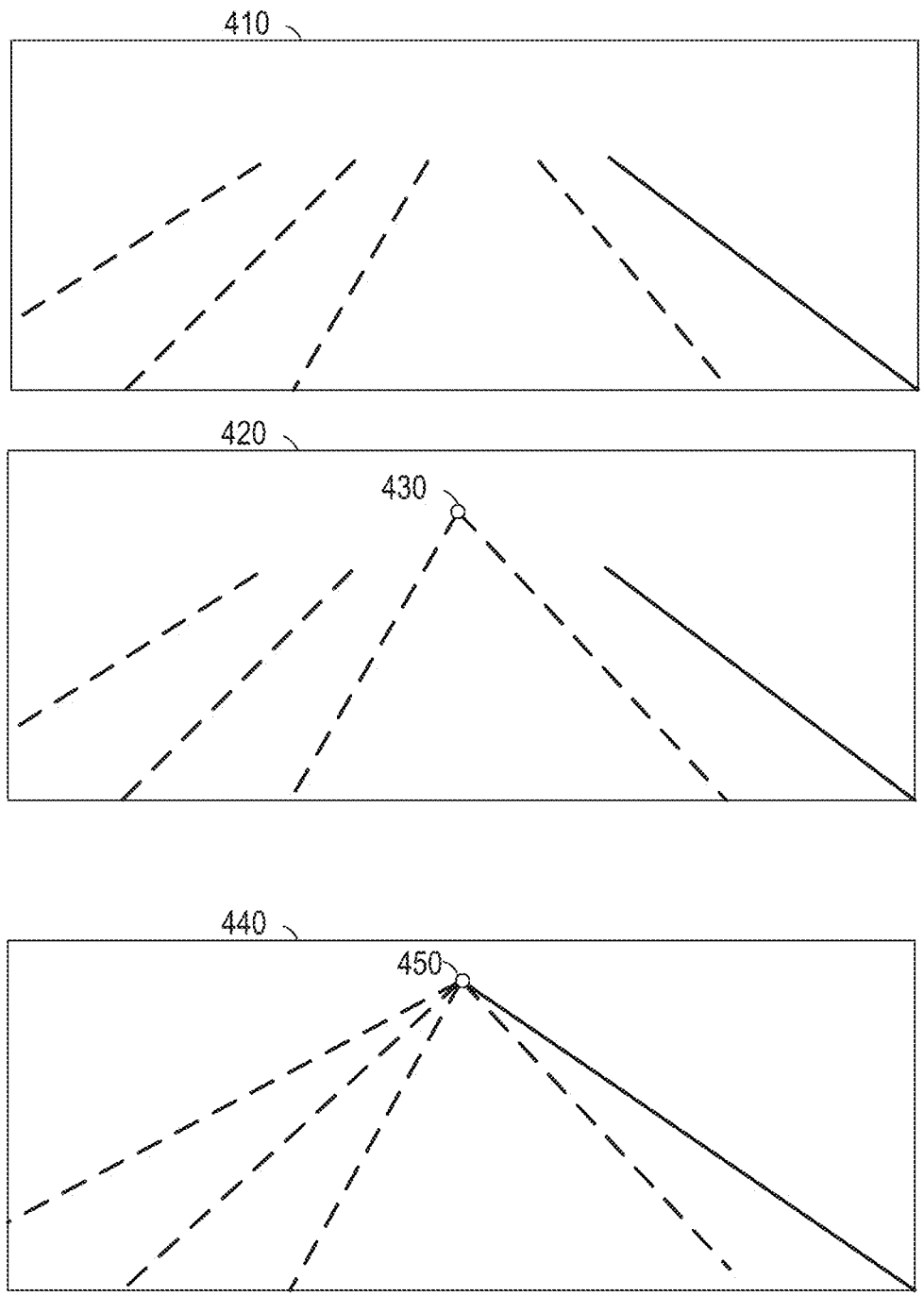
FIG. 4 is an illustration of some example primary preview points, according to some example embodiments.

FIG. 4 is an illustration of some example primary preview points, according to some example embodiments. Shown in FIG. 4 are images 410, 420, and 440 and PPPs 430 and 450. The images 410, 420, and 440 may be captured by one or more cameras integrated into the driver's vehicle. For example, the images may be captured by a single forward-facing camera integrated into the vehicle, a rotating camera mounted to the roof of the vehicle, a laser scanner integrated into the vehicle, or any suitable combination thereof. Alternatively, the images 410, 420, and 440 may be captured by an external camera and transmitted to the vehicle (e.g., via a Wi-Fi or cellular network). For example, buildings or light poles may have fixed cameras mounted to them to provide environmental images to all vehicles using the road. As another example, satellite imagery may be used.

Each of the images 410, 420, and 440 is a 2D representation of the environment of the vehicle. In some example embodiments, 3D representations of the environment are used. A 3D representation may be generated from a plurality of 2D images that capture a scene from different angles. Alternatively, a 3D representation may be generated from a 2D image in combination with a depth image. In some example embodiments, the vehicle is a virtual vehicle (e.g., in a virtual reality (VR) simulation) and a 3D representation of the environment is generated from the VR environment of the virtual vehicle.

The image 410 shows a road edge and four lane dividers. The image 420 shows the road edge and four lane dividers after the image 410 has been modified to extend two lane dividers of the vehicle's lane until they converge. The point at which the boundaries of the vehicle's lane meet is marked as PPP 430. This is referred to as a convergence point PPP. The convergence point PPP may be expanded by 1-2 degrees of arc of the driver's vision to generate a corresponding PPR.

The image 440 shows the road edge and four lane dividers after the image 410 has been modified to extend the road edge and lane dividers until they converge. The point of convergence is marked as PPP 450. The PPP 450 may be the same as the PPP 430. Alternatively, the multiple lines generated may not meet at a single point and the PPP 450 may be taken as the geometric average of the multiple convergence points. The PPPs 430 and 450 correspond to the current path of the vehicle.

The road edge and lane dividers of the images 410, 420, and 440 may be identified by a convolutional neural network (CNN) that detects lines in images. Based on the road edge and lane dividers, one or more lanes of the road may be identified, including the lane of the road occupied by the driver's vehicle. The PPPs 430 and 450 may be identified using a geometric algorithm that extends lines to determine intersection points.

Figure 5:
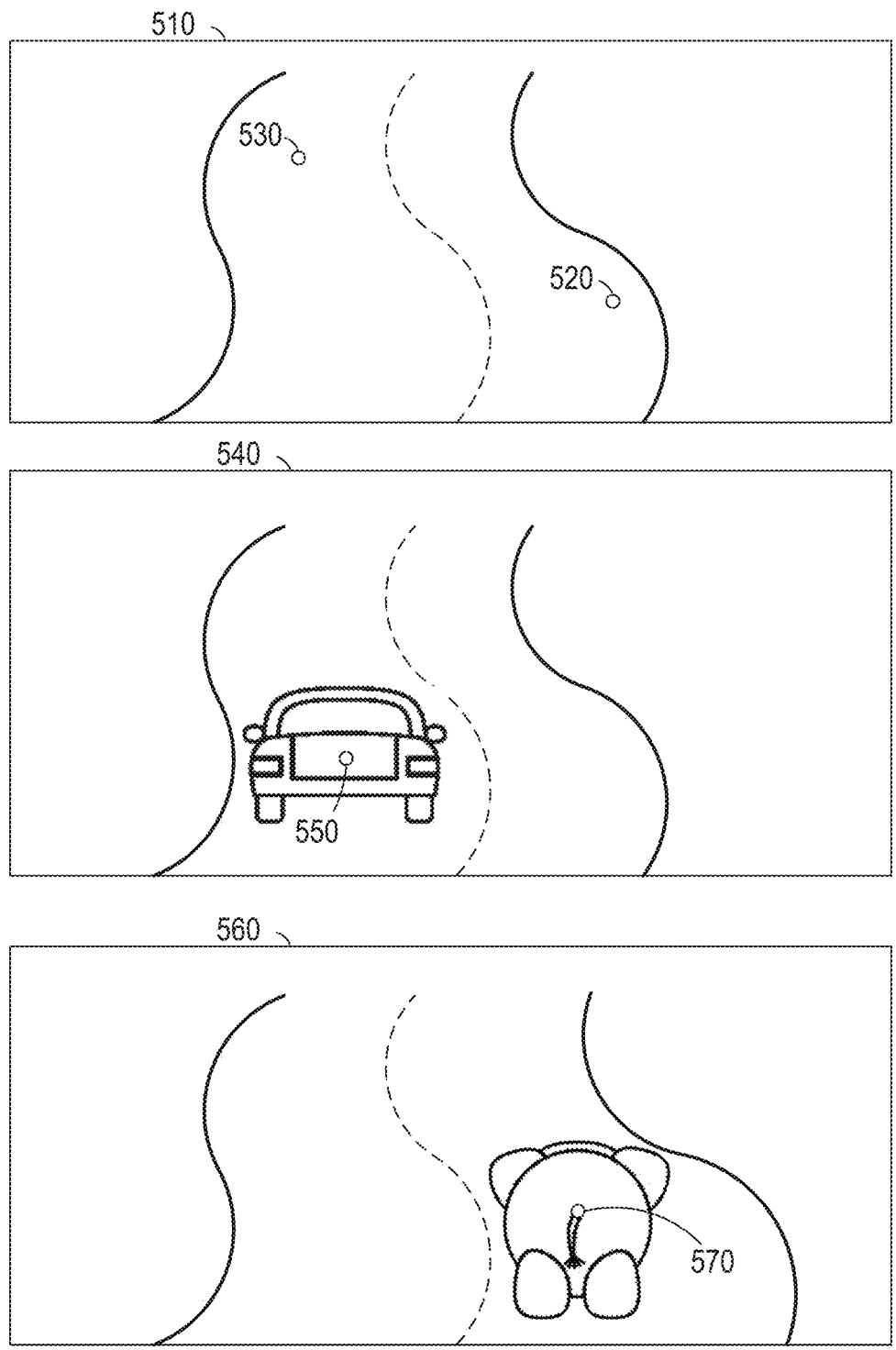
FIG. 5 is an illustration of some example primary preview points, according to some example embodiments.

FIG. 5 is an illustration of some example primary preview points, according to some example embodiments. Shown in FIG. 5 are images 510, 540, and 560 and PPPs 520, 530, 550 and 570.

The image 510 shows a curving road with PPPs 520 and 530. The PPPs 520 and 530 are curve point PPPs that indicate points on the road to which attention should be paid to enable the driver to steer properly through the curve. The curve point PPP may be the center of a curving lane at the point at which the tangent of the curve is parallel to the direction of motion of the vehicle. The curve point PPP may be expanded by 1-2 degrees of arc of the driver's vision to generate a corresponding PPR (e.g., an elliptical or circular PPR).

The image 540 shows the curving road with a PPP 550. The PPP 550 is an object PPP that indicates a car in front of the vehicle to which attention should be paid to enable the driver to avoid collision with the vehicle. The object PPP may be at the center of the object. The object PPR may be expanded from the object PPP (e.g., in an ellipse or circle), or a bounding box (e.g., a rectangular bounding box) of the object may be used as the object PPR. The image 560 shows the curving road with a PPP 570. The PPP 570 is an object PPP that indicates an elephant in front of the vehicle.

The PPPs 520, 530, 550, and 570 may be identified through the use of a trained machine-learning algorithm (e.g., implemented using a CNN). For example, a set of training data including images of different types of objects and their labels may be provided to a machine-learning algorithm to train the machine-learning algorithm to identify objects and their locations in images. Images of an environment of a vehicle may be provided to the trained machine-learning algorithm, which generates an output that identifies the types of objects depicted and their locations. A PPP selection algorithm may identify a PPP for identified objects based on their type and location. For example, the PPP for a car may be placed at the center of the depiction of the car while the PPP for a donkey may be placed at the depiction of the donkey's head.

Figure 6:
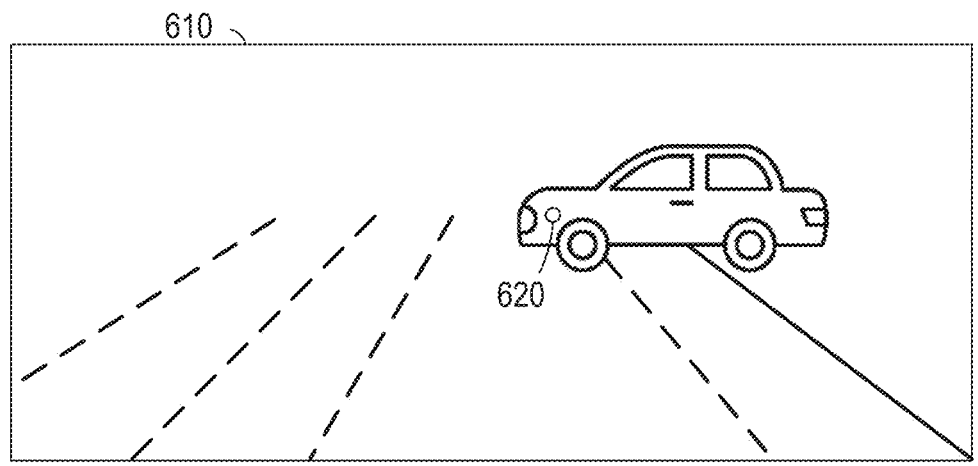
FIG. 6 is an illustration of some example primary preview points, according to some example embodiments.
Figure 6:
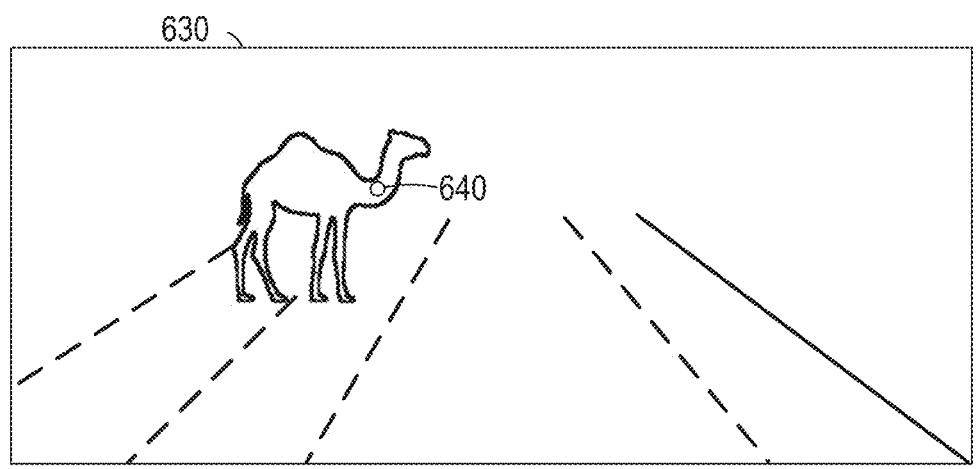

FIG. 6 is an illustration of some example primary preview points, according to some example embodiments. Shown in FIG. 6 are images 610 and 630 as well as PPPs 620 and 640. The PPPs 620 and 640 may be identified through the use of a trained machine-learning algorithm.

The image 610 shows the road of the image 410 with the addition of a car merging or crossing the road. The PPP 620 is a merging object PPP that indicates an object that is moving into the path of the vehicle. The merging object PPP may be at the center of the object, at the point of the object nearest to the path of the vehicle, or at a position between the two (as shown by the PPP 620). The merging object PPR may be expanded from the merging object PPP (e.g., by 1-2 degrees of arc of the driver's vision), or a bounding box of the merging object may be used as the merging object PPR.

The image 630 shows the road of the image 410 with the addition of a camel merging into the vehicle's lane or crossing the road. The PPP 640, like the PPP 620, is a merging object PPP.

The PPPs 620 and 640 may be determined based on multiple images of the environment of the vehicle. For example, individual images may show an object at a location, and the velocity of the object may be determined from a sequence of images. The location of the PPP within the bounding box of the object may be selected based on the velocity of the object. For example, the PPP for a stationary object may be located at the center of the bounding box, while the PPP for a fast-moving object may be located at the edge of the bounding box in the direction of movement.

The shape and size of each of the above PPRs may be determined based on a type of the PPP (e.g., a curve point PPP, a convergence PPP, an object PPP, a merging object PPP), a size of the object, a distance of the PPP from the vehicle, a present speed of the vehicle, a driver attribute, or any suitable combination thereof. The PPR may be centered around the PPP or shifted by an offset. For example, a PPR may be shifted away from or toward neighboring PPPs, shifted toward or away from neighboring lanes, or any suitable combination thereof.

Based on identification of the object, a corresponding secondary preview point (SPP) or secondary preview region (SPR) may be identified instead of a PPP or PPR. For example, a database table may map object types to priority scores (e.g., in the range 1-10). For objects having a priority score at or above a predetermined threshold (e.g., 7), detection of the object may result in a PPP or PPR. For objects having an priority score below the predetermined threshold, detection of the object may result in an SPP or SPR. Examples of objects that may be associated with priority scores below the threshold include surrounding traffic, roadside objects, and traffic signs along the road side. The SPPs and SPRs may not present an immediate impact to the ongoing driving process. Such SPPs and SPRs are not included in the distraction detection procedure since the driver is not required to pay attention to such objects.

In some example embodiments, the SPPs and SPRs are utilized for evaluation of driver's attention level. Sufficient attention given by the driver to SPRs and SPPs indicates a satisfactory attention level. For instance, tired and fatigued drivers pay less attention to such secondary objects whereas fully attentive drivers maintain higher levels of situational awareness of all surrounding objects including the SPRs and SPPs. Accordingly, failure to monitor SPPs and SPRs may be used to modify driver-specific parameters to the attention function discussed below with respect to FIG. 7.

Figure 7:
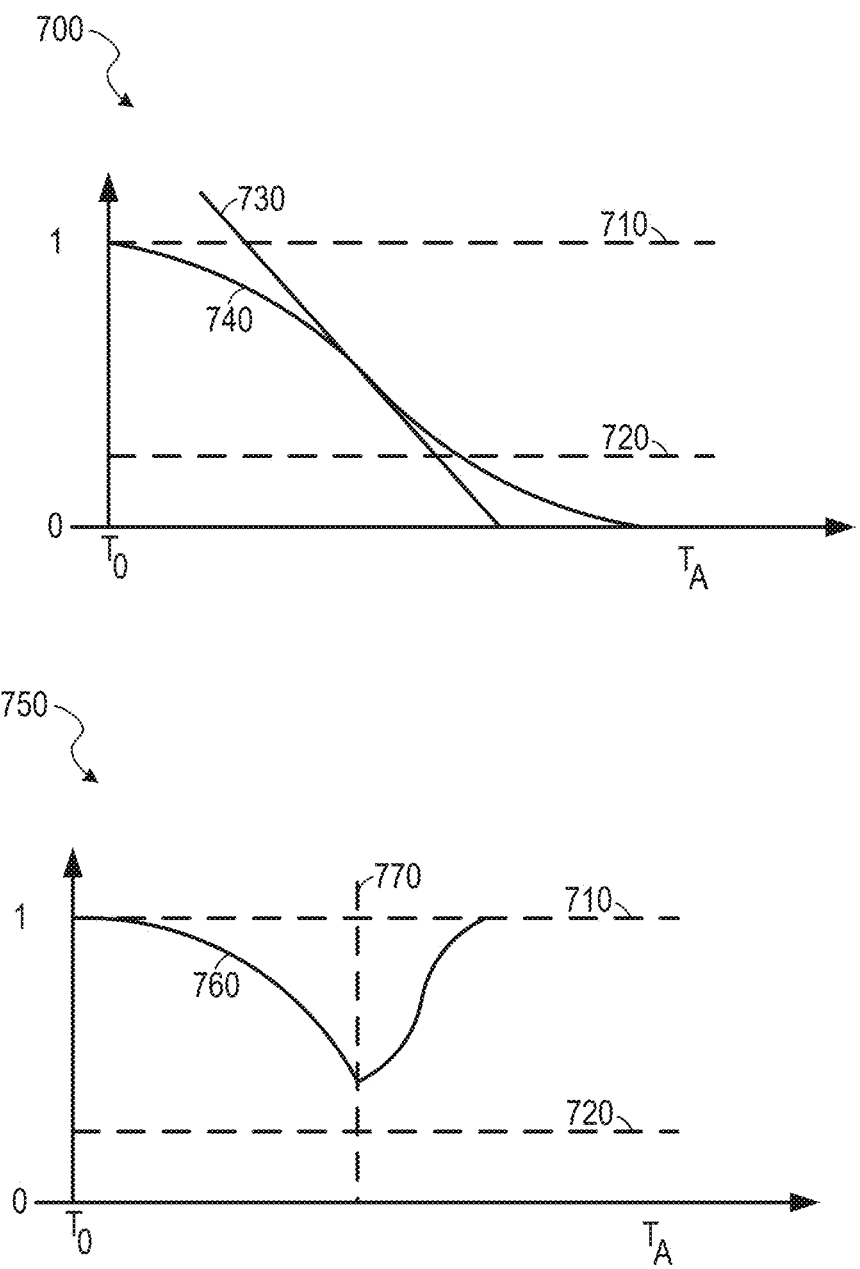
FIG. 7 is an illustration of graphs of an attention function, according to some example embodiments.

FIG. 7 is an illustration of graphs 700 and 750 of an attention function, according to some example embodiments. The graph 700 shows an attention level 740 for a PPR as a function of time. In some embodiments, a representation of a PPR may be created when a PPP is detected, as discussed above. The representation of the PPR may be associated with an attention function or another mechanism to determine a current attention level of the PPR at any point in time. The attention level may depend on (or relate to) a sequence of gaze points, dynamically changing environmental factors, or any suitable combination thereof. The environmental factors may be used as parameters of the attention function.

The attention level 710 is a maximum attention level and the attention level 720 is a predetermined threshold below which the attention level 740 should not fall. At any time t, the decaying rate is the derivative of the attention level 740 function at time t, as shown by the decaying rate 730. The graph 750 shows an attention level 760 for a PPR as a function of time. The graph 750 includes the attention levels 710 and 720 as well as a time 770 at which the driver begins paying attention to the PPR.

In the graphs 700 and 750, the attention level functions are non-linear, with the decaying rate increasing as the driver continues to not pay attention to the PPR. In some example embodiments, the attention level function is a logistic decay function. An example logistic decay function is:

$$S_v = S_v(t_0) e^{-\frac{pk|e_g|(t-t_0)}{d_0 d_1 t_A}} \qquad \text{Equation 1}$$

In equation 1, the initial value, $S_v(t_0)$ is the attention level at the time at which the driver's gaze was no longer in the PPR. In some example embodiments, $S_v$ is initialized to 1 when the PPR is created, $t_0$ is the time at which the gaze left the PPR (e.g. according to successive detections related to the PPR at two time instances $t_1$ and $t_0$, the gaze identified to be inside PPR at $t_1$ and outside PPR at $t_0$), p is the priority score of the PPR, $e_g$ is the deviation between the present gaze position and the PPR, k is a scaling factor with respect to lane deviation and vehicle stability margin, $d_0$ is an impression decaying factor that is associated with the driver, $d_1$ is a scene complexity parameter based on environmental conditions, and $t_A$ is a preview time scaling variable. In some example embodiments, k, $d_0$, and $d_1$ are equal to 1.

The preview time scaling variable may be defined as the minimum of $t_{TTR}$, $t_{TTC}$, $t_{TTG}$, $t_p$, where $t_{TTR}$ (time to reach) is the time to reach the future PPP based on the relative position and motion of the vehicle and the PPP, $t_{TTC}$ (time to cross) is the time for the PPP to reach the lane of the vehicle, $t_{TTG}$ (time to go) is predicted time when the vehicle will accelerate (e.g., after stopping for a stop sign or light), and $t_p$ (time to preview) is a preview time constant based on the driver's characteristics.

In some example embodiments, an inexperienced driver has a larger value for $d_0$ than an experienced driver. The value for $d_1$ may be increased when one or more high-velocity (e.g., with velocity exceeding 50 miles per hour) objects are present or when the driver is found to be ignoring SPPs and SPRs.

The value of k may be object-specific based on a priority assigned to the PPP. For example, a priority may be assigned to each PPP based on distance from the vehicle, such that PPPs nearer to the vehicle have a higher priority In the graph 700, the attention level 740 decays while the driver does not focus on the PPR until it reaches 0. When the attention level 740 crosses the attention level 520, an alert is generated.

In the graph 750, the attention level 760 decays while the driver does not focus on the PPR until time 770, when the driver's attention returns. After time 770, the attention level 760 increases until it reaches the maximum attention level 710. Since the attention level 760 never reaches the attention level 720, no alert is generated.

Once the driver's gaze goes inside a PPR, $S_v$ starts recovering back to 1 following a recovering function. The recovering rate is slow initially. But $S_v$ can recover sharply once driver's gaze resides in the PPR for a minimal period of time. The attention level recovery rate can be designed with a recovery function similar to the decaying function but with a positive increasing rate. An example recovering function is a logistic growing function:

$$S_v = 1 + (S_v(t_0) - 1)e^{-\frac{cp(t-t_0)}{d_0 d_1 t_p}} \qquad \text{Equation 2}$$

Equation 2 uses the same constants and variables as equation 1, but $t_0$ of the recovering function is the time at which the driver's gaze returns to the PPR, c is a scaling factor for the recovering function, which may be the same as or different from the scaling factor k used for the decay function, and p is a priority score of the PPR. Over a period of time in which the driver's attention is divided between PPRs, the attention level for each PPR will be adjusted by alternating between application of the decay function (while the driver's gaze is outside of the PPR) and the recovering function (while the driver's gaze is in the PPR).

The two equations above include parameters such as k, the scaling factor with respect to lane deviation and vehicle stability margin, $d_0$, the impression decaying factor that is associated with the driver, $d_1$, the scene complexity parameter based on environmental conditions, and $t_A$, the preview time scaling variable. In some example embodiments, one or more of these parameters is used to determine a dynamic threshold for generating an alert. For example, the threshold for generating an alert may be higher for a poorer driver (as measured by $d_1$) or in a less-stable vehicle (as measured by k).

Figure 8:
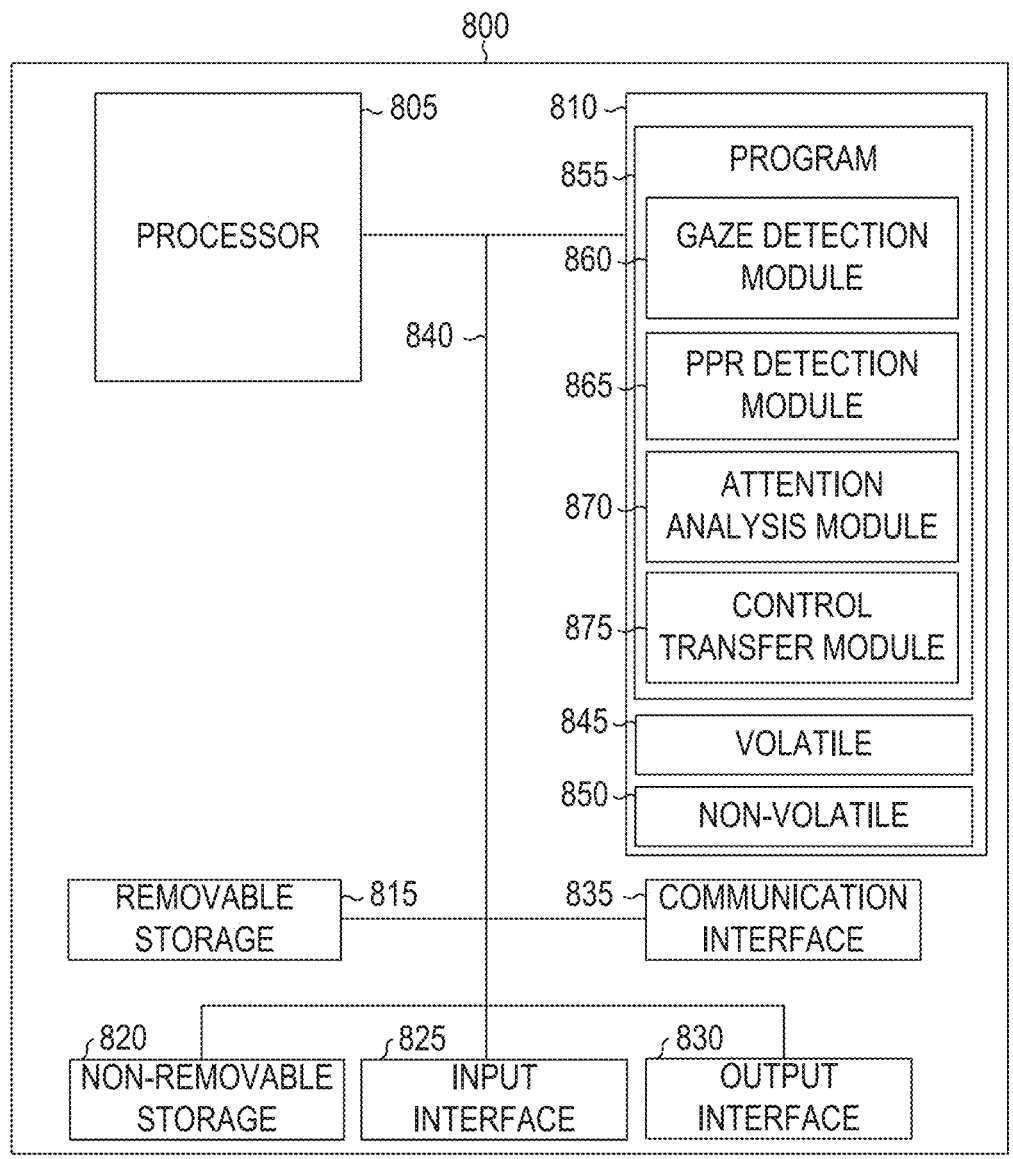
FIG. 8 is a block diagram illustrating circuitry for a device that implements algorithms and perform methods, according to some example embodiments.

FIG. 8 is a block diagram illustrating circuitry for implementing algorithms and performing methods, according to example embodiments. All components need not be used in various embodiments. For example, clients, servers, autonomous systems, network devices, and cloud-based network resources may each use a different set of components, or, in the case of servers for example, larger storage devices.

One example computing device in the form of a network device 800 (also referred to as a computer 800, a computing device 800, and a computer system 800) may include a processor 805, memory storage 810, removable storage 815, and non-removable storage 820, all connected by a bus 840. Although the example computing device is illustrated and described as the computer 800, the computing device may be in different forms in different embodiments. For example, the computing device may instead be a smartphone, a tablet, a smartwatch, or another computing device including elements the same as or similar to those illustrated and described with regard to FIG. 8. Devices such as smartphones, tablets, and smartwatches are generally collectively referred to as "mobile devices" or "user equipment." Further, although the various data storage elements are illustrated as part of the computer 800, the storage may also or alternatively include cloud-based storage accessible via a network, such as the Internet, or server-based storage.

The memory storage 810 may include volatile memory 845 and non-volatile memory 850, and may store a program 855. The computer 800 may include, or have access to a computing environment that includes, a variety of computer-readable media, such as the volatile memory 845, the non-volatile memory 850, the removable storage 815, and the non-removable storage 820. Computer storage includes random-access memory (RAM), read-only memory (ROM), erasable programmable read-only memory (EPROM) and electrically erasable programmable read-only memory (EEPROM), flash memory or other memory technologies, compact disc read-only memory (CD ROM), digital versatile disks (DVD) or other optical disk storage, magnetic cassettes, magnetic tape, magnetic disk storage or other magnetic storage devices, or any other medium capable of storing computer-readable instructions.

The computer 800 may include or have access to a computing environment that includes an input interface 825, an output interface 830, and a communication interface 835. The output interface 830 may interface to or include a display device, such as a touchscreen, that also may serve as an input device. The input interface 825 may interface to or include one or more of a touchscreen, a touchpad, a mouse, a keyboard, a camera, one or more device-specific buttons, one or more sensors integrated within or coupled via wired or wireless data connections to the computer 800, and other input devices. The computer 800 may operate in a networked environment using the communication interface 835 to connect to one or more remote computers, such as database servers. The remote computer may include a personal computer (PC), server, router, switch, network PC, peer device or other common network node, or the like. The communication interface 835 may connect to a local-area network (LAN), a wide-area network (WAN), a cellular network, a WiFi network, a Bluetooth network, or other networks.

Though the computer 800 is shown as having a single one of each element 805-865, multiples of each element may be present. For example, multiple processors 805, multiple input interfaces 825, multiple output interfaces 830, and multiple communication interfaces 835 may be present. In some example embodiments, different communication interfaces 835 are connected to different networks.

Computer-readable instructions stored on a computer-readable medium (e.g., the program 855 stored in the memory storage 810) are executable by the processor 805 of the computer 800. A hard drive, CD-ROM, and RAM are some examples of articles including a non-transitory computer-readable medium such as a storage device. The terms "computer-readable medium" and "storage device" do not include carrier waves to the extent that carrier waves are deemed too transitory. "Computer-readable non-transitory media" includes all types of computer-readable media, including magnetic storage media, optical storage media, flash media, and solid-state storage media. It should be understood that software can be installed in and sold with a computer. Alternatively, the software can be obtained and loaded into the computer, including obtaining the software through a physical medium or distribution system, including, for example, from a server owned by the software creator or from a server not owned but used by the software creator. The software can be stored on a server for distribution over the Internet, for example.

The program 855 is shown as including a gaze detection module 860, a PPR detection module 865, an attention analysis module 870, and a control transfer module 875. Any one or more of the modules described herein may be implemented using hardware (e.g., a processor of a machine, an ASIC, an FPGA, or any suitable combination thereof). Moreover, any two or more of these modules may be combined into a single module, and the functions described herein for a single module may be subdivided among multiple modules. Furthermore, according to various example embodiments, modules described herein as being implemented within a single machine, database, or device may be distributed across multiple machines, databases, or devices.

The gaze detection module 860 processes one or more images of the face of a driver of a vehicle to determine the gaze of the driver. The images of the face of the driver may be received via the input interface 825 from the driver-facing camera 120. Existing methods for determining a gaze estimation point in two-dimensional or three-dimensional space may be used to determine the driver's gaze. For example, a ray may be determined for each eye that has its origin in the center of the eye and passes through the pupil of the eye. The point at which the rays intersect is the driver's three-dimensional gaze point. To determine the two-dimensional gaze point, a ray is generated with its origin at the midpoint between the two eyes and terminating at the three-dimensional gaze point. The intersection of this ray with a two-dimensional projection of an image of an environment is the driver's two-dimensional gaze point.

The PPR detection module 865 processes one or more representations of an environment of a vehicle to identify PPRs. For example, images of the environment may be received via the input interface 825 from one or more exterior-facing cameras or 3D representations of the environment may be generated based on the images received from the exterior-facing cameras. Objects in the representation of the environment can appear and disappear from time to time. They may also vary in appearance (e.g., size and position). In order to determine that an object in a current representation of the environment is the same object as in a previous representation of the environment, object tracking is used. First, objects are detected in each representation of the environment is received. Second, through position and motion continuity conditions, objects are tracked in the temporal domain to associate a detected object in the current representation of the environment to the previous instances of the same object. Kalman filter and object tracking algorithm (like DSST) are typically used. Features can also be used to associate and recognize object through online learning. For example, since a new object can appear only from a scene boundary or from certain occluded image regions, any recognized object that is not adjacent to a boundary or occluded image region should have a corresponding object in the previous representation of the environment. A new object cannot be associated to any of the previous observed objects and will be classified and registered in the distraction detection algorithm. Similarly, an existing PPP-associated object can only disappear via a scene boundary or by occlusion. After a certain predetermined period of time (e.g., 30 seconds), an object that disappears will be removed from the object registration list. Accordingly, the associated PPR of the object, if any, will be deleted.

The attention analysis module 870 compares the detected gaze of the driver to the PPRs to determine if the driver is paying sufficient attention to each PPR. If the attention level for one or more PPRs drops below a predetermined threshold, the attention analysis module 870 causes an alert to be generated. For example, the output interface 830 may trigger a speaker in the vehicle to make an audible alert or a haptic feedback device in a steering wheel to vibrate.

The control transfer module 875 transfers control of an automated vehicle between computer and human control. The control transfer module 875 may confirm, via the attention analysis module 870, that a human driver is paying sufficient attention to all PPRs before transferring control.

FIG. 9 is a block diagram illustrating a database schema 900 suitable for gaze-based driver detection using primary preview regions, according to some example embodiments. The database schema 900 includes a PPP table 905, a PPR table 920, an attention level table 935, and a driver table 950. The PPP table 905 uses a table definition 910 and includes rows 915A, 915B, and 915C. The PPR table 920 uses a table definition 925 and includes rows 930A, 930B, and 930C. The attention level table 935 uses a table definition 940 and includes rows 945A, 945B, and 945C. The driver table 950 uses a table definition 955 and includes rows 960A and 960B.

Each of the rows 915A-915C of the PPP table 905 stores information for a PPP. According to the table definition 910, each of the rows 915A-915C includes an identifier, a location, and a type. The identifier may be a unique identifier for the PPP and may be used to relate information stored in different tables. The location may be a 2D or 3D location stored using relative or absolute positioning (e.g., latitude, longitude, and elevation). In the example PPP table 905, the positions are stored as 3D locations using relative positioning from the front center of the vehicle, measured in meters. The type indicates whether the PPP represents a vehicle, a curve, a sign, a vanishing point, an animal, a pedestrian, or any other type of point to which the driver should pay attention.

Each of the rows 930A-930C of the PPR table 920 stores information for a PPR. According to the table definition 925, each of the rows 930A-930C includes an identifier, a relative PPP location, and a size. In some example embodiments, each PPR corresponds to exactly one PPP, allowing the same identifier to be used for the PPR and its corresponding PPP. The relative PPP location indicates the position of the PPP within the PPR. The relative PPP location may be stored as a type indicator as shown in the example PPR table 920, indicating whether the PPP is located at the center or edge (e.g., the edge closest to the driver's vehicle or the edge at the front of a direction of movement of the PPP). Alternatively, the relative PPP location may be stored as a 2D or 3D offset from the center of the PPR. The size stores the size of the PPR, for example by providing a radius of a sphere or circle. Alternatively, the size may store a bounding box or bounding cube for the PPR.

The attention level table 935 stores the rows 945A-945C, each of which includes an identifier, an attention level, a gaze status, a time of last attention change, and a transition attention level. The identifier indicates the identifier of the PPR to which the attention level data of the row applies. The attention level indicates the current attention level for the corresponding PPR. The gaze status indicates whether the driver's gaze point is currently in the PPR. The time of last attention change indicates the time at which the driver's gaze point last entered or left the PPR. The transition attention level indicates the transition level for the PPR at the time of last attention change. In example embodiments in which Equations 1 and 2 are used to determine the driver's attention level, the equation to use may be selected based on the gaze status, the time of last attention change may be used as the value for $t_0$, and the transition attention level may be used as the value for $S_v(t_0)$.

The driver table 950 stores the rows 960A-960B, each of which includes a Boolean value indicating whether the driver is currently active, set to True if the row stores data for the current driver and False otherwise, and a reaction coefficient for the driver. Additional data may be stored in the driver table 950. For example, a photo of the driver may be stored so that the driver can be identified by image recognition based on one or more images captured by the driver-facing camera 140. In example embodiments in which Equations 1 and 2 are used to determine the driver's attention level, the driver's reaction coefficient may be used as the value for k.

Figure 10:
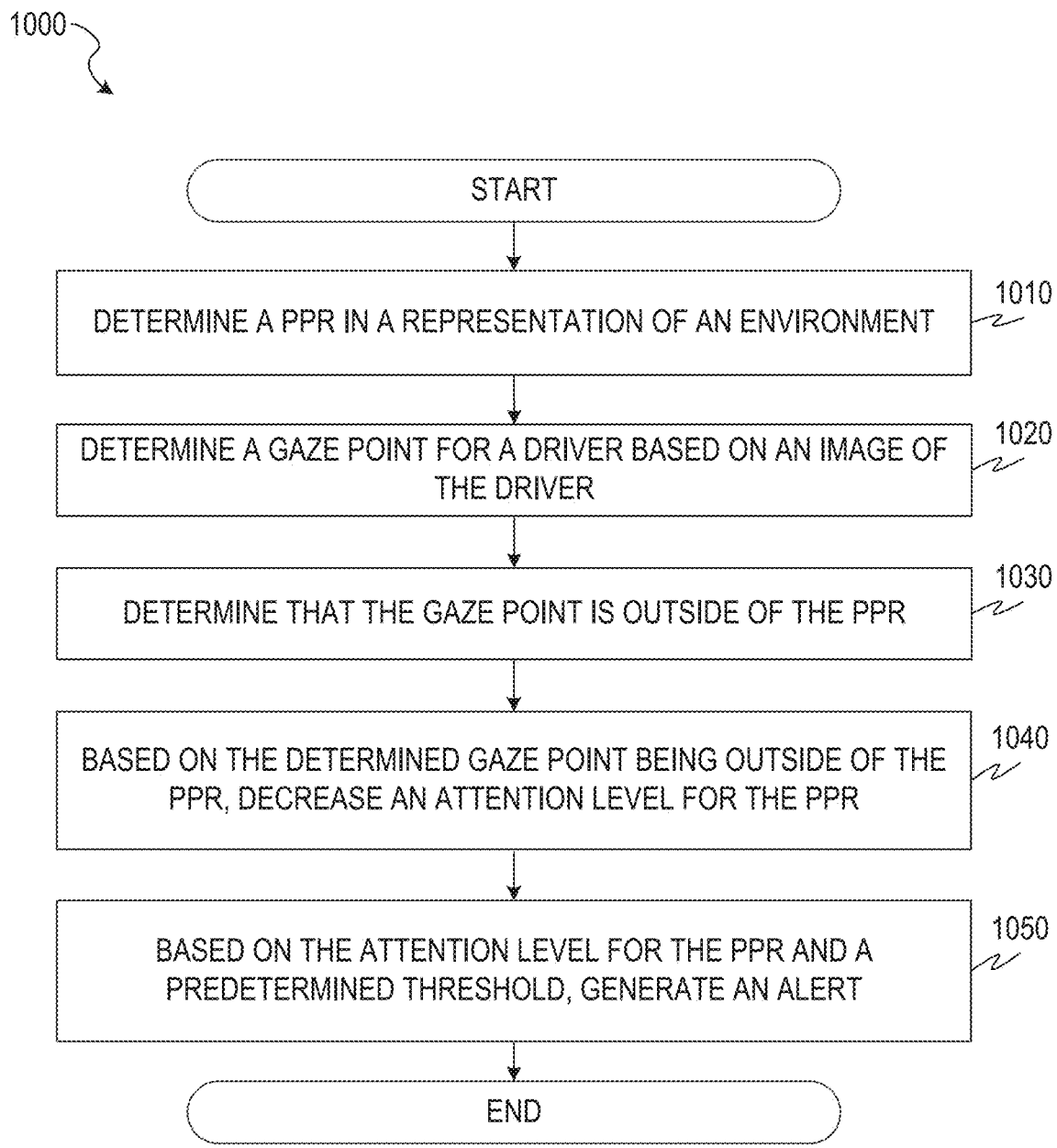
FIG. 10 is a flowchart illustration of a method of gaze-based driver detection using primary preview regions, according to some example embodiments.

FIG. 10 is a flowchart illustration of a method 1000 of gaze-based driver detection using primary preview regions, according to some example embodiments. The method 1000 includes operations 1010, 1020, 1030, and 1040. By way of example and not limitation, the method 1000 is described as being performed by elements of the computer 800, described above with respect to FIG. 8, integrated into a vehicle (e.g., a vehicle including the windshield 110 and the driver-facing camera 120 of FIG. 1).

In operation 1010, the PPR detection module 865 determines a PPR in a representation of an environment. For example, an object identification algorithm may identify an object depicted in an image of an environment and determine a PPP for the object. Based on the PPP and a classification of the object, the PPR in the representation of the environment may be determined. In some example embodiments, the PPR for an object is the bounding box for the object. In other example embodiments, the PPR is a cube or sphere centered on the object.

In operation 1020, the gaze detection module 860 determines a gaze point for a driver based on an image of the driver. For example, the image of the driver may depict the pupils of the driver's eyes as well as the driver's head. Using calibration data or statistical data, the center of the driver's eyes may be estimated and a ray may be determined for each eye that has its origin in the center of the eye and passes through the pupil of the eye. The point at which the rays intersect is the driver's three-dimensional gaze point. To determine the two-dimensional gaze point, a ray is generated with its origin at the midpoint between the two eyes and terminating at the three-dimensional gaze point. The intersection of this ray with a two-dimensional projection of an image of an environment is the driver's two-dimensional gaze point.

In operation 1030, the attention analysis module 870 determines that the gaze point is outside of the PPR. For example, the 3D gaze point may be compared with the volume of a 3D PPR to determine if the gaze point is within or outside of the PPR. As another example, the 2D gaze point may be compared with the area of a 2D PPR to determine if the gaze point is within or outside of the PPR.

In operation 1040, the attention analysis module 870, based on the determined gaze point being outside of the PPR, decreases an attention level for the PPR. For example, whether the driver's gaze is within the PPR may be used to adjust the attention level for the PPR as shown in FIG. 5.

In operation 1050, the attention analysis module 870 generates an alert based on the attention level for the PPR and a predetermined threshold. For example, using a normalized attention level with a range from 0 to 1, the predetermined threshold may be 0.2. If the attention level for the PPR falls below the predetermined threshold, an alert is generated.

Using the method 1000, a driver is alerted when the attention level for a detected object is insufficient. By repeating the operations 1020-1040 for all detected objects, the driver is alerted if any object is not paid sufficient attention. For example, in a complex situation involving multiple vehicles, animals, signs, and curves, a driver may inadvertently focus excessively on a subset of the PPRs needing attention. In this situation, the method 1000 will provide an alert regarding the PPRs being ignored, possibly preventing an accident.

Figure 11:
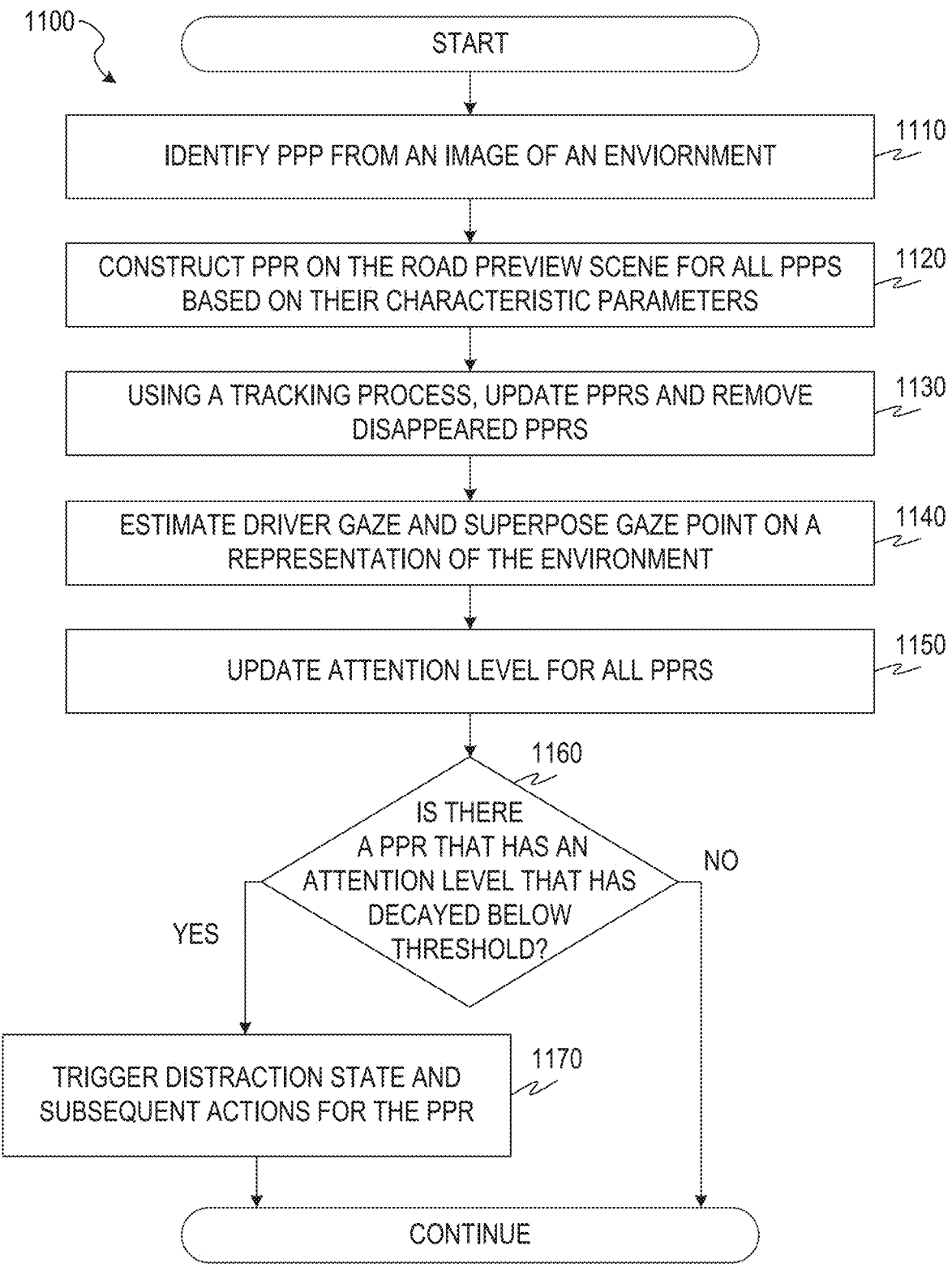
FIG. 11 is a flowchart illustration of a method of gaze-based driver detection using primary preview regions, according to some example embodiments.

FIG. 11 is a flowchart illustration of a method 1100 of gaze-based driver detection using primary preview regions, according to some example embodiments. The method 1100 includes operations 1110, 1120, 1130, 1140, 1150, 1160, and 1170. By way of example and not limitation, the method 1100 is described as being performed by elements of the computer 800, described above with respect to FIG. 8, integrated into a vehicle (e.g., the vehicle 200 including the windshield 310 and the driver-facing camera 140 as shown in FIGS. 1-3).

In operation 1110, the PPR detection module 865 identifies a PPP from an image of an environment (e.g., an image captured by a front-facing camera). For example, a trained machine learning algorithm may take the image as an input image and identify a location and class of an object depicted in the image.

In operation 1120, the PPR detection module 865 constructs a PPR on the image for all PPPs based on their characteristic parameters. The characteristic parameters may be accessed from a database based on the class of the object associated with the PPP. For example, a PPR generated from a PPP associated with a large vehicle class may be larger than a PPR generated from a PPP associated with a small animal class.

In operation 1130, the PPR detection module 865 updates PPRs and removes disappeared PPRs using a tracking process. The tracking process tracks the object from one image to another so that as the object moves relative to the camera capturing the images, the object is maintained as a single object rather than being treated as a distinct object in each image. Thus, the PPRs for moving objects are maintained, and any previously-stored PPRs for objects no longer viewed are removed.

In some example embodiments, the PPR detection module 865 estimates a future path using vehicle and road information. For example, the vehicle speed, current direction, lane, turn signal, and angle of the steering wheel may be used to determine an estimated future path for the vehicle. The PPR detection module 865 may determine that a PPR is not along the future path and, based on the determination that the first PPR is not along the future path, remove the first PPR. For example, a PPR for a bicycle to the left of the vehicle that is heading away from the vehicle may be determined to not be on the path of the vehicle when the vehicle is in a right-turn lane with right-turn signal activated. As a result, the PPR for the bicycle may be deleted, such that no alert will be generated even if the driver never focuses on the bicycle.

In operation 1140, the gaze detection module 860 estimates the driver's gaze point and superposes the gaze point on a representation of the environment (e.g., the image of the environment or a 3D representation of the environment generated from the image of the environment and other data). This superposition enables, in operation 1150, the attention analysis module 870 to determine which PPRs, if any, the driver is currently focusing on. In operation 1150, the attention analysis module 870 updates the attention level for each PPR based on the determination of the driver's focus (e.g., increasing the attention level for a PPR the driver is focusing on and decreasing the attention level for all other PPRs).

In some example embodiments, a gaze region is used instead of a gaze point. The gaze region may be defined as a circle or sphere centered on the gaze point with a radius determined based on a mean error for the estimation of the gaze point. In some example embodiments, the gaze region is defined as an ellipse centered on the gaze point with major and minor radii determined based on directional mean errors (e.g., yaw and pitch mean errors) for the estimation of the gaze point.

In operation 1160, the attention analysis module 870 determines if any PPRs have attention levels that have fallen below a predetermined threshold. For each PPR for which the attention level has fallen below the predetermined threshold, the attention analysis module 870, in operation 1170, triggers a distraction state and takes actions that result from the distraction state. For example, an alert may be generated. After operation 1170 is performed (or skipped, if no PPRs have attention levels that are below the predetermined threshold), the method 1100 continues by returning to operation 1110 and repeating the method 1100 with updated image data. For example, the method 1100 may be performed every 200 ms to monitor the driver's attention level.

Figure 12:
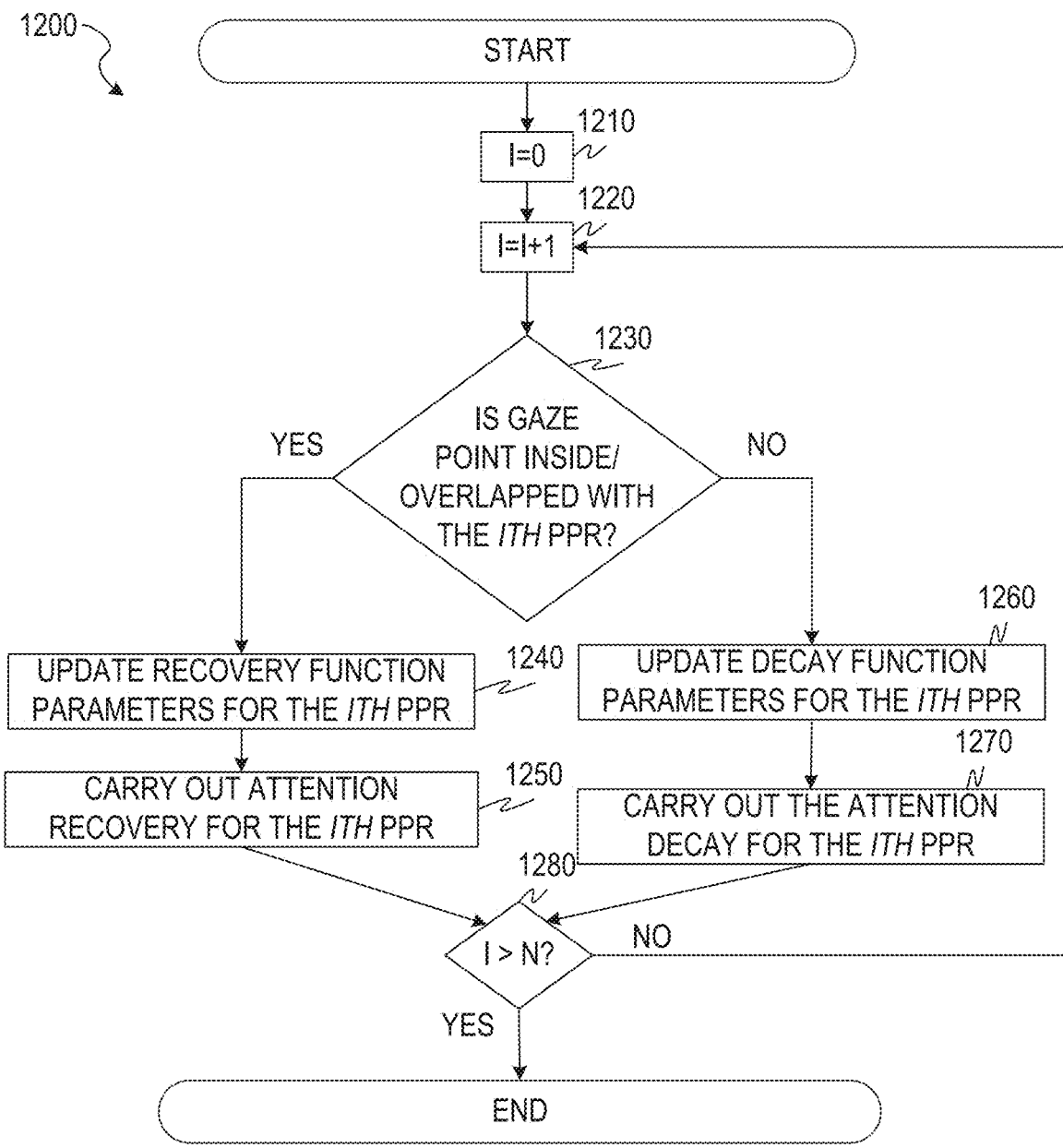
FIG. 12 is a flowchart illustration of a method of gaze-based driver detection using primary preview regions, according to some example embodiments.

FIG. 12 is a flowchart illustration of a method 1200 of gaze-based driver detection using primary preview regions, according to some example embodiments. The method 1200 includes operations 1210, 1220, 1230, 1240, 1250, 1260, 1270, and 1280. By way of example and not limitation, the method 1200 is described as being performed by elements of the computer 800, described above with respect to FIG. 8, integrated into a vehicle (e.g., the vehicle 200 including the windshield 310 and the driver-facing camera 140 as shown in FIGS. 1-3). The method 1200 is an example implementation of the operation 1150 of the method 1100. Additionally or alternatively, the method 1200 may be executed periodically (e.g., every 100 ms).

In operation 1210, the attention analysis module 870 initializes a loop variable, i, to 0. In operation 1220, the attention analysis module 870 increments the loop variable.

In operation 1230, the attention analysis module 870 determines if the current PPR (corresponding to the loop variable i) encompasses the driver's gaze point. If the current PPR does encompass the driver's gaze point, the method 1200 continues with operation 1240. Otherwise, the method 1200 continues with operation 1260.

In operation 1240, the attention analysis module 870 updates recovery function parameters for the current PPR. For example, using Equation 2 (described above with respect to FIG. 5) as the recovering function, the value of $(t-t_0)$, the length of time the driver has continuously gazed at the PPR, may be updated. In operation 1250, the attention analysis module 870 re-evaluates the recovery function, increasing the attention level for the PPR.

In operation 1260, performed if the driver's gaze point is not within the current PPR, the attention analysis module 870 updates decay function parameters for the current PPR. In some example embodiments, the decay function parameters are the same as the recovery function parameters. Alternatively, the recovery function and the decay function may be distinct equations with distinct parameters. In operation 1270, attention analysis module 870 carries out attention decay for the current PPR. Thus, the attention level for the PPR is decreased.

After the performance of operation 1250 or operation 1270, the attention analysis module determines if all PPRs have been evaluated (operation 1280). If some PPRs remain, control returns to operation 1220. Thus, the attention level for all PPRs will be updated by execution of the method 1200. Once all PPRs have ben processed, the method 1200 completes and attention levels for all PPRs have been updated.

Figure 13:
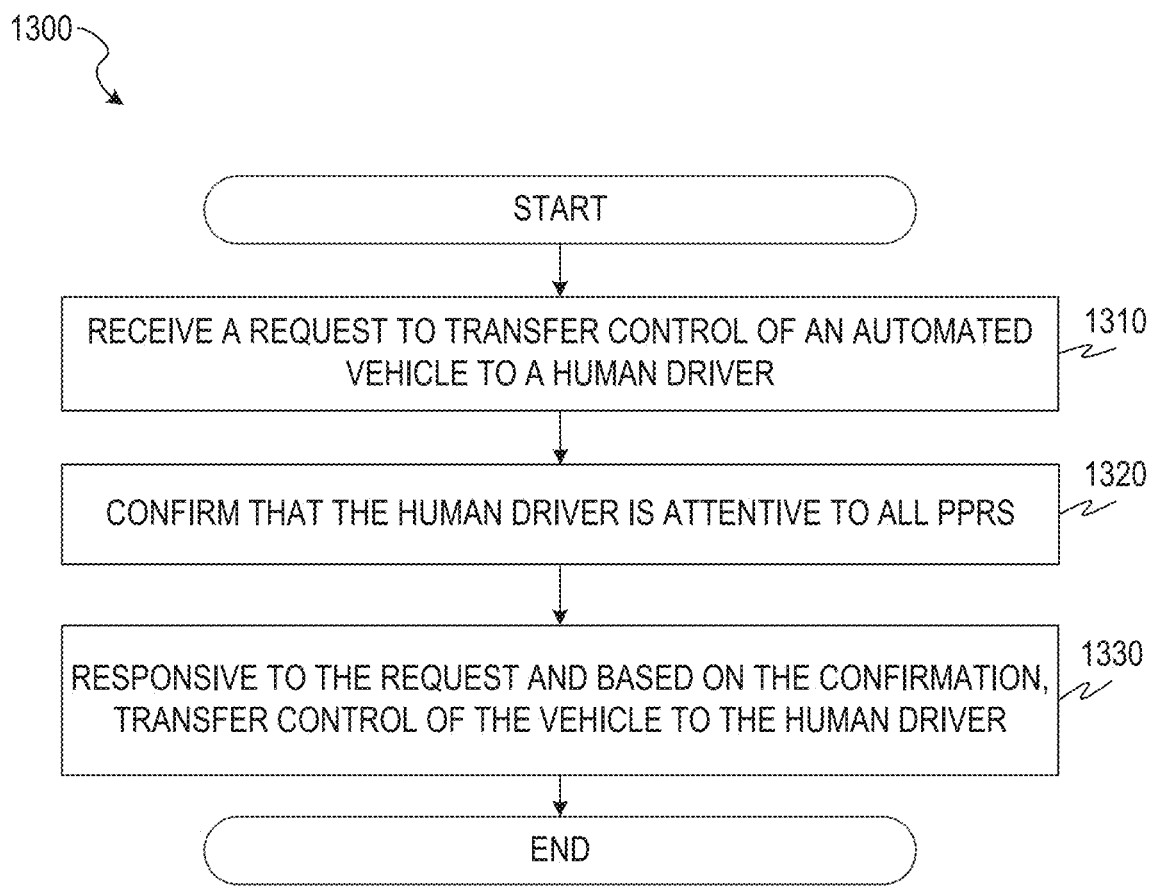
FIG. 13 is a flowchart illustration of a method of transferring control of an automated vehicle to a human driver, according to some example embodiments.

FIG. 13 is a flowchart illustration of a method 1300 of transferring control of an automated vehicle to a human driver, according to some example embodiments. The method 1300 includes operations 1310, 1320, and 1330. By way of example and not limitation, the method 1300 is described as being performed by elements of the computer 800, described above with respect to FIG. 8, integrated into a vehicle (e.g., the vehicle 200 including the windshield 310 and the driver-facing camera 140 as shown in FIGS. 1-3).

In operation 1310, the control transfer module 875 receives a request to transfer control of an automated vehicle to a human driver. For example, the driver may press a button on a steering wheel, issue a voice command, tap a brake pedal, or otherwise indicate to the automated vehicle that the driver wishes to take control.

In operation 1320, the control transfer module 875 confirms that the human driver is attentive to all PPRs. The confirmation may be realized through communication with the attention analysis module 870. For example, the driver's attention level to all PPRs may be determined for a predetermined period of time (e.g., 15 seconds). If, during the predetermined period of time, no attention level is allowed to fall below a threshold at which an alert is generated, the method 1300 continues with operation 1330. Otherwise, the predetermined period of time is restarted and monitoring of the driver's attention level to all PPRs is resumed. In some example embodiments, the method 1300 is terminated if the driver's attention level to any PPR is insufficient.

In operation 1330, the control transfer module 875 transfers control of the vehicle to the human driver in response to the request and based on the confirmation. The transfer of control may include disengaging automatic control of the vehicle, providing an alert to the driver indicating that manual control has been engaged, or any suitable combination thereof.

Use of the method 1300 may improve the safety of transferring control of an automated vehicle to a human driver by ensuring that the driver is paying adequate attention to the road and any obstacles or hazards. Additionally, use of the method 1300 may avoid accidental transfer of control (e.g., by the driver accidentally pressing a button or otherwise providing a transfer control request), since the accidental request is unlikely to be accompanied by sufficient attention from the driver.

Although a few embodiments have been described in detail above, other modifications are possible. For example, the logic flows depicted in the figures do not require the particular order shown, or sequential order, to achieve desirable results. Other steps may be provided in, or steps may be eliminated from, the described flows, and other components may be added to, or removed from, the described systems. Other embodiments may be within the scope of the following claims.

What is claimed is:

1. A computer-implemented method of detecting distracted driving comprising:
   determining, by one or more processors, a primary preview region (PPR) in a representation of an environment;
   determining, by the one or more processors, a first gaze point for a driver based on a first sequence of images of the driver;
   determining, by the one or more processors, that the first gaze point is inside of the PPR;
   based on the first gaze point being inside of the PPR and a reaction coefficient of the driver, increasing, by the one or more processors, an attention level for the PPR using a first function;
   determining, by the one or more processors, a second gaze point based on a second sequence of images of the driver;
   determining, by the one or more processors, that the second gaze point is outside of the PPR;
   based on the second gaze point being outside of the PPR and the reaction coefficient of the driver, decreasing, by the one or more processors, the attention level for the PPR using a second function different from the first function; and
   based on the decreased attention level for the PPR, generating, by the one or more processors, an alert.

2. The method of claim 1, wherein:
   the PPR is a first PPR and is one of a plurality of PPRs, each PPR of the plurality of PPRs having a corresponding attention level;
   the generating of the alert is further based on the attention level for each PPR of the plurality of PPRs; and
   the method further comprises:
      estimating a future path using vehicle and road information;
      determining that the first PPR is not along the future path; and
      based on the determination that the first PPR is not along the future path, removing the first PPR from the plurality of PPRs.

3. The method of claim 2, further comprising:
   determining a priority score for each PPR of the plurality of PPRs; and
   wherein the attention level for each PPR of the plurality of PPRs is based on the priority score for the PPR.

4. The method of claim 1, further comprising:
   identifying an object depicted in the representation of the environment by analyzing the representation with a trained machine-learning algorithm.

5. The method of claim 1, wherein the determining of the PPR comprises:
   determining a primary preview point (PPP); and
   determining the PPR based on the PPP and a predetermined radius.

6. The method of claim 1, wherein the determining of the PPR in the representation of the environment comprises identifying a lane of a road.

7. The method of claim 1, wherein the representation of the environment is generated by a laser scanner.

8. The method of claim 1, wherein the generating of the alert comprises generating an audio alert.

9. The method of claim 1, wherein the generating of the alert comprises generating a haptic alert.

10. The method of claim 1, wherein the generating of the alert comprises activating brakes of a vehicle.

11. The method of claim 1, wherein the generating of the alert comprises altering a direction of a vehicle.

12. The method of claim 1, wherein the determining of the attention level for the PPR is based on a skill level of the driver.

13. The method of claim 1, wherein the generating of the alert is further based on a predetermined threshold.

14. A system for detecting distracted driving, comprising:
   a memory storage comprising instructions; and
   one or more processors in communication with the memory, wherein the one or more processors execute the instructions to perform:
      determining a primary preview region (PPR) in a representation of an environment;
      determining a first gaze point for a driver based on a first sequence of images of the driver;
      determining that the first gaze point is inside of the PPR;
      based on the first gaze point being inside of the PPR and a reaction coefficient of the driver, increasing an attention level for the PPR using a first function;
      determining a second gaze point based on a second sequence of images of the driver;
      determining that the second gaze point is outside of the PPR;
      based on the second gaze point being outside of the PPR and the reaction coefficient of the driver, decreasing the attention level for the PPR using a second function different from the first function; and
      based on the decreased attention level for the PPR, generating an alert.

15. A non-transitory computer-readable medium that stores instructions that, when executed by one or more processors, cause the one or more processors to perform operations comprising:
   determining a first primary preview region (PPR) in a representation of an environment;
   determining a first gaze point for a driver based on a first sequence of images of the driver;
   determining that the first gaze point is inside of the PPR;
   based on the first gaze point being inside of the PPR and a reaction coefficient of the driver, increasing an attention level for the PPR using a first function;
   determining a second gaze point based on a second sequence of images of the driver;
   determining that the second gaze point is outside of the PPR;
   based on the second gaze point being outside of the PPR and the reaction coefficient of the driver, decreasing the attention level for the PPR using a second function different from the first function; and
   based on the decreased attention level for the PPR , generating an alert.

16. The system of claim 14, wherein:
   the PPR is a first PPR and is one of a plurality of PPRs, each PPR of the plurality of PPRs having a corresponding attention level;
   the generating of the alert is further based on the attention level for each PPR of the plurality of PPRs; and
   the one or more processors further execute the instructions to perform:
      estimating a future path using vehicle and road information;
      determining that the first PPR is not along the future path; and based on the determination that the first PPR is not along the future path, removing the first PPR from the plurality of PPRs.

17. The computer-implemented method of claim 1, wherein:
the first function is a logistic decay function; and
the second function is a logistic growing function.

18. The computer-implemented method of claim 17, wherein:
a scaling factor of the logistic decay function is different than a scaling factor of the logistic growing function.

19. The computer-implemented method of claim 1, further comprising:
determining a second PPR in the representation of the environment;
determining that the first gaze point is inside of the second PPR; and
based on the first gaze point being inside of the second PPR, increasing a second attention level for the second PPR using the first function.

* * * * *